(12) United States Patent
Luo et al.

(10) Patent No.: US 8,324,382 B2
(45) Date of Patent: Dec. 4, 2012

(54) CRYSTALLINE FORMS OF PEMETREXED DIACID, AND PREPARATIONS THEREOF

(75) Inventors: Jie Luo, Chongqing (CN); Meng Lin, Chongqing (CN); Zhengyong Zhu, Chongqing (CN); Junlai Luo, Chongqing (CN); Wenrun Ye, Chongqing (CN); Yongmei Qin, Chongqing (CN); Jie Deng, Chongqing (CN)

(73) Assignee: Chongqing Pharmaceutical Research Institute Co., Ltd., Chongqing (CN)

( * ) Notice: Subject to any disclaimer, the term of this patent is extended or adjusted under 35 U.S.C. 154(b) by 0 days.

(21) Appl. No.: 13/120,080

(22) PCT Filed: Sep. 21, 2009

(86) PCT No.: PCT/CN2009/074059
§ 371 (c)(1),
(2), (4) Date: Mar. 21, 2011

(87) PCT Pub. No.: WO2010/031357
PCT Pub. Date: Mar. 25, 2010

(65) Prior Publication Data
US 2011/0172424 A1    Jul. 14, 2011

(30) Foreign Application Priority Data
Sep. 22, 2008 (CN) .......................... 2008 1 0070345

(51) Int. Cl.
C07D 487/04 (2006.01)
(52) U.S. Cl. ...................................... 544/280
(58) Field of Classification Search ........... 544/280
See application file for complete search history.

(56) References Cited

U.S. PATENT DOCUMENTS

| 5,106,974 | A | 4/1992 | Akimoto et al. |
| 5,344,932 | A | 9/1994 | Taylor |
| 5,416,211 | A | 5/1995 | Barnett et al. |
| 5,539,113 | A | 7/1996 | Akimoto et al. |
| 6,262,262 | B1 | 7/2001 | Kjell |
| 7,138,521 | B2 | 11/2006 | Chelius et al. |
| 2001/0011142 | A1 | 8/2001 | Kjell |
| 2003/0032666 | A1* | 2/2003 | Van Der Schaaf et al. ... 514/419 |
| 2003/0216416 | A1 | 11/2003 | Chelius et al. |
| 2008/0045711 | A1 | 2/2008 | Busolli et al. |
| 2008/0059244 | A1 | 3/2008 | Fujita et al. |

FOREIGN PATENT DOCUMENTS

| CN | 1055182 | 10/1991 |
| CN | 1778797 | 5/2006 |
| CN | 1827604 | 9/2006 |
| CN | 1840530 | 10/2006 |
| EP | 0432677 | 6/1991 |
| WO | 01/14379 | 3/2001 |
| WO | 01/62760 | 8/2001 |
| WO | 2008/021405 | 2/2008 |
| WO | 2008/021410 | 2/2008 |
| WO | 2008/124485 | 10/2008 |
| WO | 2010/028105 | 3/2010 |

OTHER PUBLICATIONS

Jian eet al, 2003, Chinese Journal of Geochemistry, Vo I. 22, No. 1, p. 38-44.*
Guo, Zhi-Xiong, Wang, He-Fang, Xin, Chun-Wei, Chen, Li-Gong, Synthesis of Antifolate Alimta, Chinese Journal of Organic Chemistry, vol. 26, No. 4, p. 546-550. 2006. School of Chemical Engineering, Tianjin University, Tianjin 300072.
Zhao Dong-Mei, Tang Cheng-Zuo, Shi Tao, Cheng Mao-Sheng, Synthesis of a multitargeted antifolate-pemetrexed, Chinese Journal of Medicinal Chemistry, vol. 18, No. 6, p. 445-448. Dec. 2008. School of Pharmaceutical Engineering, Shenyang Pharmaceutical University, Shenyang 110016, China.
Charles J. Barnett, et al "A Practical Synthesis of Multitargeted Antifolate LY231514" Organic Process Research & Development 1999, 3, pp. 184-188.
European Search Report dated May 11, 2012 (PCT Application No. PCT/CN2009/074059.

* cited by examiner

Primary Examiner — Golam M M Shameem
Assistant Examiner — Karen Cheng
(74) Attorney, Agent, or Firm — Workman Nydegger

(57) ABSTRACT

Three new crystalline forms of pemetrexed diacid, preparation methods and uses thereof are disclosed. These preparation processes are simple and have better practicality.

7 Claims, 3 Drawing Sheets

CRYSTALLINE FORMS OF PEMETREXED DIACID, AND PREPARATIONS THEREOF

This application claims the priority of Chinese Patent Application No. 200810070345.9, filed with the State Intellectual Property Office of the People's Republic of China on Sep. 22, 2008, entitled "new crystalline forms of pemetrexed diacid, and preparations thereof", the entire content of which is hereby incorporated by reference.

FIELD OF THE INVENTION

The present invention relates to the fields of organic chemistry and pharmacy. Specifically, the present invention relates to new crystalline forms of a folic acid antagonist, N-[4-[2-(2-amino-4,7-dihydro-4-oxo-1H-pyrrolo[2,3-d]pyrimidin-5-yl)ethyl]benzoyl]-L-glutamic acid (formula I, i.e. Pemetrexed diacid), and preparation thereof.

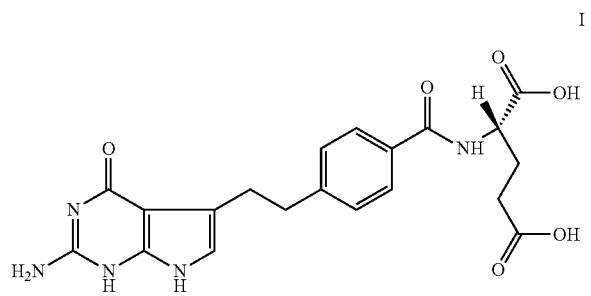

BACKGROUND OF THE INVENTION

Pemetrexed diacid and derivatives thereof act as a multi-targeted antifolate that strongly inhibit various folate-dependent enzymes, including thymidylate synthase (TS), dihydrofolate reductase (DHFR), glycinamide ribonucleotide formyltransferase (GARFT) and the like, and have excellent anti-tumor activities. At present, the disodium salt, i.e., pemetrexed disodium has already been marketed in USA, the European Union, Canada, China, Japan etc., which is used for treating malignant pleural mesothelioma as a first-line drug, and treating non-small cell lung cancer as a first-line or second-line drug. In the treatment of malignant pleural mesothelioma, pemetrexed disodium is the only chemotherapeutic agent in the market currently. In the second-line treatment of non-small cell lung cancer, pemetrexed disodium has a comparative efficacy and low toxicities compared with the standard drug docetaxel, therefore, it is promising for pemetrexed disodium to become a new standard drug for the second-line treatment of non-small cell lung cancer. In addition, the clinical studies of pemetrexed disodium in the treatment of tumors of breast, bowel, pancreatic, head and neck, gastric, bladder and the like are ongoing, and the results are worthy of expectation.

Pemetrexed diacid is an essential precursor for the preparation of pemetrexed disodium, and the quality of pemetrexed diacid plays a key role in the preparation of pemetrexed disodium. Therefore, the physical and chemical properties of pemetrexed diacid have been recently studied in more detail. The polymorphism of pemetrexed diacid has drawn more attention, for example, U.S. patent No. US20080045711 disclosed seven crystalline forms of pemetrexed diacid, including two crystalline forms of hydrate (crystalline forms A, B), one crystalline form of DMSO solvate (crystalline form C), two crystalline forms of N,N-dimethyl formamide solvate (crystalline forms D, E), and two crystalline forms of anhydrate (crystalline forms F, G). Among these crystalline forms, solvents incorporated in crystalline forms C, D, and E have higher boiling points, wherein the boiling point is 189° for DMSO and 156° for N,N-dimethyl formamide. In the further preparation of pemetrexed disodium, the solvent with high boiling point may be introduced into final product, resulting in the increased burden of controlling organic residual in final product. Anhydrous crystalline forms F and G are obtained after drying at a higher temperature)(160~200°) which may result in a certain extent of degradation of pemetrexed diacid, being adverse to the purity of product. Although the hydrate crystalline forms A and B overcome the disadvantages mentioned above, they have the following defects: the yield of crystalline A is quite low (about 40%) resulting in a low practical use; the time for preparing crystalline form B is quite long, wherein it takes about 18 hr only for the crystallizing step, which is unfavorable for the increase of the production efficiency. Thus, in order to overcome the shortcomings of crystalline forms of pemetrexed diacid in the prior art, we performed further studies on the polymorphism of pemetrexed diacid. Surprisingly, we have discovered several new crystalline forms of pemetrexed diacid. The methods for preparing these new crystalline forms are simple and practical, which are in favor of the further preparation of pemetrexed disodium.

SUMMARY OF THE INVENTION

An object of the present invention is to provide new crystalline forms of pemetrexed diacid which are prepared simply and practicably, as well as preparation methods thereof.

In order to achieve this object, the present invention provides three new crystalline forms of N-[4-[2-(2-amino-4,7-dihydro-4-oxo-1H-pyrrolo[2,3-d]pyrimidin-5-yl)ethyl]benzoyl]-L-glutamic acid (pemetrexed diacid) with certain X-ray powder diffraction patterns (respectively referred to crystalline forms H, I, and J).

The X-ray powder diffraction pattern of crystalline form H of pemetrexed diacid provided in the present invention is characterized by the following: the position of diffraction peaks at 2θ are found at around 9.9°, 12.2°, 16.1°, 18.9°, 19.8°, 22.6° and 25.1°, furthermore, the position of diffraction peaks at 2θ are also found at around 6.4°, 10.6°, 17.1°, 18.1°, 21.1°, 25.8°, 27.8°, 30.1° and the like. Crystalline form H of pemetrexed diacid is characterized by the X-ray powder diffraction pattern as shown in FIG. 1.

Crystalline form H of pemetrexed diacid provided in the present invention is a crystalline form of hydrate with a water content of 5-80%.

The crystalline form content (mass content) of pemetrexed diacid crystalline form H provided in the present invention is usually more than 80%, preferably more than 90%.

Crystalline form I of pemetrexed diacid provided in the present invention is characterized by the X-ray powder diffraction pattern as shown in FIG. 2.

Crystalline form I of pemetrexed diacid provided in the present invention is a crystalline form of hydrate with a water content of 5 wt-80 wt %.

The crystalline form content (mass content) of pemetrexed diacid crystalline form I provided in the present invention is usually more than 80%, preferably more than 90%.

Crystalline form J of pemetrexed diacid hydrate provided in the present invention is characterized by the X-ray powder diffraction pattern as described below: the position of diffraction peaks at 2θ are found at around 12.2°, 20.3°, 21.3°, 28.9°, 32.8°, furthermore, the position of diffraction peaks at 2θ are also found at around 5.6°, 8.9°, 18.4°, 19.5°, 23.3°, 24.5°, 25.7°, 27.7°, 31.4°, 34.2° and the like. Crystalline form J of pemetrexed diacid is characterized by the X-ray powder diffraction pattern as shown in FIG. 3. Crystalline form J of pemetrexed diacid has a water content of 5 wt-80 wt %.

The crystalline form content (mass content) of crystalline form J of pemetrexed diacid hydrate provided in the present invention is usually more than 80%, preferably more than 90%.

X-ray powder diffraction analysis in the present invention was carried out by PW1710 BASED X-ray diffractometer with CuKα radiation source (α=1.5406 Å) at an ambient temperature of 0-40° C. and an ambient humidity of 30%-80%. Water content in the present invention was determined using Karl Fischer moisture titrator (METTLER TOLEDO DL31).

Representative X-ray powder diffraction patterns of crystalline forms H, I, and J of pemetrexed diacid provided in the present invention are shown in accompanying figures. As used herein, "representative X-ray powder diffraction pattern" means that the X-ray powder diffraction characteristics of the crystalline form are consistent with the overall shape of diffraction peaks in the pattern. It is understood that the position and intensity of peaks in the X-ray powder diffraction pattern determined for the same crystalline form may vary to some extent due to a number of factors such as particle size of samples tested, processing of samples, equipments, testing parameters, and operation. In some cases, certain diffraction peaks may even not found substantially. This difference means that the experimental error of 2θ values of diffraction peaks may be ±0.4°, usually ±0.2°.

The present invention also provides methods for preparing the above three new crystalline forms of pemetrexed diacid.

The present invention provides a method for preparing crystalline form H of pemetrexed diacid, comprising crystallizing pemetrexed diacid from the mixed solution containing pemetrexed diacid and water as well as water-miscible solvent. In particular, dissolving pemetrexed salt (including dry or wet product) in a mixed solvent consisting of water and water-miscible solvent, and adjusting pH value thereof to 1-2.5 to crystallize pemetrexed diacid; or dissolving directly pemetrexed diacid in a mixed solvent consisting of water and water-miscible solvent to crystallize.

As used in the method for preparing crystalline form H, "pemetrexed salt" means pemetrexed salts with a certain water-solubility, which includes, but not limited to, sodium salt of pemetrexed, lithium salt of pemetrexed, potassium salt of pemetrexed, ammonium salt of pemetrexed, calcium salt of pemetrexed, and the like. Disodium pemetrexed is preferred.

As used in the method for preparing crystalline form H, "water-miscible solvent" includes ethanol, methanol, isopropanol, acetone, acetonitrile, tetrahydrofuran, ethylene glycol dimethyl ether and the like, or a mixture thereof, and wherein ethanol and acetone are preferred. The volume of "water-miscible solvent" is usually as 0.5-3 fold as that of water, and preferably as 0.8-1.5 fold as that of water. The volume of water is usually as 3-30 fold as the weight of pemetrexed salt or pemetrexed diacid, and preferably as 3-20 fold.

As used in the method for preparing crystalline form H, "pH value adjustment" is achieved by adding acids, which include, but not limited to, hydrochloric acid, hydrobromic acid, hydroiodic acid, sulfuric acid, phosphoric acid, sodium bisulfate, sodium dihydrogen phosphate, formic acid, acetic acid, oxalic acid, trifluoroacetic acid, methanesulfonic acid, p-toluenesulfonic acid, benzoic acid, and the like. Hydrochloric acid and acetic acid are preferred. The acid used is usually an aqueous solution of an acid after dilution by water, with a typical concentration of 0.5-5 mol/L, and the pH value thereof is adjusted to the range of 1-3. The temperature of system at the end of pH adjustment is usually Detween room temperature to near boiling point of the mixed solution.

As used in the method for preparing crystalline form H, when "pemetrexed diacid is directly dissolved in a mixed solvent consisting of water and water-miscible solvent", dissolution may be promoted by adjusting pH value or heating, wherein pH value is usually adjusted to 1-3 and heating temperature is usually from 40° C. to near boiling point of the mixed solution.

In the method for preparing crystalline form H, crystallization is usually carried out with stirring for 0.2-6 hr, preferably for 0.3-2 hr. The temperature at the end of crystallization is usually between 0° to room temperature. In order to improve yield of crystallization, a certain amount of water can be added during crystallization, wherein the volume of water added is usually as 0.5-4 fold as the initial volume of water.

The resulting crystal of Pemetrexed diacid in the method for preparing crystalline form H can be separated by conventional methods in the art, such as filtration. The water content of crystalline form H collected is usually 40 wt~80 wt %. This crystal can be further dried to decrease its water content, usually under the condition of reduced pressure, typically 0.075~0.098 MPa, at the temperature of 35~70° for 10-40 hr. The water content of crystalline form H is usually 5 wt~10 wt % after dryness.

The present invention provides a method for preparing crystalline form I of pemetrexed diacid, comprising adjusting pH value of aqueous solution of pemetrexed salt with a concentration of less than 0.07 mol/L to a pH of 2-3 using an acid, and then crystallizing pemetrexed diacid.

As used in the method for preparing crystalline form I, "pemetrexed salt" means a pemetrexed salt with a certain of water-solubility, which includes, but not limited to, sodium salt of pemetrexed, lithium salt of pemetrexed, potassium salt of pemetrexed, ammonium salt of pemetrexed, calcium salt of pemetrexed, and the like. The disodium salt of pemetrexed is preferred.

As used in the method for preparing crystalline form I, the concentration of pemetrexed salt recited in "aqueous solution of pemetrexed salt with a lower concentration" is usually lower than 0.07 mol/L, and the pH value of the solution is usually 7-14. The preparation method of this aqueous solution comprises dissolving pemetrexed salt in an aqueous solution or alkali solution, or dissolving pemetrexed diacid in an aqueous alkali solution, or using an aqueous solution containing pemetrexed salt. As used above, the "alkali" in "an aqueous alkali solution" includes, but not limited to, sodium hydroxide, potassium hydroxide, ammonium hydroxide, lithium hydroxide, calcium hydroxide, sodium carbonate, potassium carbonate, sodium phosphate, potassium phosphate, disodium hydrogen phosphate, dipotassium hydrogen phosphate, and the like; as well as mixture thereof, preferably sodium hydroxide and potassium hydroxide. The aqueous alkali solution may further comprise a certain amount of water-miscible solvent, such as ethanol, methanol, isopropanol, acetone, acetonitrile, tetrahydrofuran, ethylene glycol dimethyl ether and the like, or mixture thereof. The volume thereof is usually as 0.05-1 fold as that of the aqueous solution.

The acid used in adjusting pH value in the method for preparing crystalline form I includes, but not limited to, hydrochloric acid, hydrobromic acid, hydroiodic acid, sulfuric acid, phosphoric acid, sodium bisulfate, sodium dihydrogen phosphate, formic acid, acetic acid, oxalic acid, trifluoroacetic acid, methanesulfonic acid, p-toluenesulfonic acid, benzoic acid and the like, and mixture thereof. Hydrochloric acid and acetic acid are preferred. The temperature at which adjusting pH value and crystallization is performed is usually −10° to 40°, preferably 0° to room temperature. Crystallization is usually carried out with stirring for 0.1-3 hr, preferably for 0.3-1 hr.

The resulting crystalline form I of pemetrexed diacid in the method for preparing crystalline form I can be separated by conventional methods in the art, such as filtration. The water content of pemetrexed diacid crystal collected is usually 40 wt~80 wt %. This crystal can be further dried to decrease its water content, usually under the condition of reduced pressure, typically 0.075~0.098 MPa, at a temperature of 35~70° C. for 10-40 hr. The water content of crystalline form I of pemetrexed diacid is usually 5 wt~10 wt % after dryness.

The present invention provides a method for preparing crystalline form J of pemetrexed diacid, comprising adjusting pH value of an aqueous solution of pemetrexed salt with a concentration of higher than 0.07 mol/L to a pH of 2-4 using an acid, and then crystallizing pemetrexed diacid.

As used in the method for preparing crystalline form J, "pemetrexed salt" means pemetrexed salts with a certain of water-solubility, which includes, but not limited to, sodium salt of pemetrexed, lithium salt of pemetrexed, potassium salt of pemetrexed, ammonium salt of pemetrexed, calcium salt of pemetrexed, and the like, and preferably disodium salt of pemetrexed.

As used in the method for preparing crystalline form J, the concentration of pemetrexed salt recited in "aqueous solution of pemetrexed salt with a higher concentration" is usually higher than 0.07 mol/L, and the pH value of the solution is usually 7-14. The preparation method of this aqueous solution comprises dissolving pemetrexed salt in an aqueous solution or alkali solution, or dissolving pemetrexed diacid in an aqueous alkali solution, or using an aqueous solution containing pemetrexed salt. As used above, the "alkali" in "an aqueous alkali solution" includes, but not limited to, sodium hydroxide, potassium hydroxide, ammonium hydroxide, lithium hydroxide, calcium hydroxide, sodium carbonate, potassium carbonate, sodium phosphate, potassium phosphate, disodium hydrogen phosphate, dipotassium hydrogen phosphate, and the like; as well as mixture thereof, preferably sodium hydroxide and potassium hydroxide. The aqueous alkali solution may further comprise a certain amount of water-miscible solvent, such as ethanol, methanol, isopropanol, acetone, acetonitrile, tetrahydrofuran, ethylene glycol dimethyl ether and the like, or mixture thereof. The volume thereof is usually as 0.05-2 fold as that of the aqueous solution.

The acid used in adjusting pH value in the method for preparing crystalline form J includes, but not limited to, hydrochloric acid, hydrobromic acid, hydroiodic acid, sulfuric acid, phosphoric acid, sodium bisulfate, sodium dihydrogen phosphate, formic acid, acetic acid, oxalic acid, trifluoroacetic acid, methanesulfonic acid, p-toluenesulfonic acid, benzoic acid and the like, and mixture thereof Hydrochloric acid and acetic acid are preferred. The temperature at which adjusting pH value and crystallization is performed is usually −10° to 40°, preferably 0° to room temperature During the crystallization, the solution may also be heated or cooled to promote crystal growth. The heating temperature is usually 50-70° and the cooling temperature is usually 0° to room temperature. Crystallization is usually carried out with stirring for 0.1-5 hr, preferably for 0.3-2 hr.

The resulting crystalline form J of pemetrexed diacid in the method for preparing crystalline form J can be separated by conventional methods in the art, such as filtration. The water content of pemetrexed diacid crystal collected is usually 40 wt~80 wt %. This crystal can be further dried to decrease its water content, usually under the condition of reduced pressure, typically 0.075~0.098 MPa, at a temperature of 35~70° C. for 10-40 hr. The water content of crystalline form J of pemetrexed diacid is usually 5 wt~10 wt % after dryness.

Another object of the present invention is to provide the use of the three above new crystalline forms of pemetrexed diacid in the preparation of a pharmaceutically acceptable salt of pemetrexed diacid.

This use comprises reacting the three above new crystalline forms of pemetrexed diacid with corresponding alkali to obtain pharmaceutically acceptable salt of pemetrexed diacid. This use further comprises preparing the new crystalline forms of pemetrexed diacid of the present invention using the methods provided in the present invention and then reacting with corresponding alkali to obtain pharmaceutically acceptable salt of pemetrexed diacid.

The present invention also provides a method for preparing pemetrexed salt, comprising the steps of adding pemetrexed diacid into an aqueous solvent, dissolving pemetrexed diacid with corresponding alkali; adding appropriate organic solvent miscible with water after dissolution to crystallize a pharmaceutically acceptable salt of pemetrexed diacid; or performing lyophilization to obtain a pharmaceutically acceptable salt of pemetrexed diacid in freeze-dried form. The aqueous solvent includes water, and a mixed solvent of water with an organic solvent miscible with water.

"A pharmaceutically acceptable salt of pemetrexed diacid" in the method described above includes sodium salt, potassium salt, lithium salt, ammonium salt, and the like of pemetrexed diacid, preferably disodium pemetrexed.

"Corresponding alkali" in the method described above includes sodium hydroxide, potassium hydroxide, ammonium hydroxide, lithium hydroxide, calcium hydroxide, sodium carbonate, potassium carbonate, sodium phosphate, potassium phosphate, disodium hydrogen phosphate, dipotassium hydrogen phosphate, and the like, preferably sodium hydroxide.

The molar amount of "corresponding alkali" added for the dissolution of pemetrexed diacid in the above mentioned method is usually more than 2 fold of that of pemetrexed diacid. The pH value is adjusted after dissolution depending on the pemetrexed salt prepared, for example, the pH value is usually adjusted to 7-12 when preparing disodium pemetrexed.

"Appropriate organic solvent miscible with water" recited in "adding appropriate organic solvent miscible with water after dissolution" in the above mentioned method includes ethanol, acetone, acetonitrile, isopropanol, tetrahydrofuran, ethylene glycol dimethyl ether and the like, as well as the mixture thereof, preferably ethanol, acetone and acetonitrile. The volume of organic solvent added is usually as 2-10 fold as that of water. The pemetrexed salt precipitated can be separated by conventional methods in the art, such as filtration. Pemetrexed salt collected can be further dried.

For the above method, when performing lyophilization after dissolution to obtain a pharmaceutically acceptable salt of pemetrexed diacid in freeze-dried form, "appropriate organic solvent miscible with water" in "aqueous solvent" should be suitable for lyophilization, and includes t-butanol, dimethyl sulfoxide, dioxane and the like, as well as the mixture thereof. Dispersant such as mannitol, lactose, fructose and the like may also be added in the solution before lyophilization in order to improve lyophilization.

Pemetrexed diacid and pemetrexed disodium used in the present invention are prepared according to the method disclosed in patent CN200410097284.7.

Overall, the three new crystalline forms of pemetrexed diacid (crystalline forms H, I, and J) provided in the present invention have good reproducibility and can be prepared in a simple and practical way, and thus they are improved crystalline forms of pemetrexed diacid.

DETAILED DESCRIPTION OF THE PRESENT INVENTION

The present invention will be further illustrated hereinafter in combination with the following examples. These examples are provided to make the present invention better understood by those skilled in the art, but are not intended to restrict the scope of the present invention in any way. It should be noted that these examples are based on laboratory scale, thus certain parameters in the process may vary when scaling up, as understood by those skilled in the art. The terms and abbreviations used in the examples have their common meanings. For example, "g", "ml", "mol/L", "°", and "MPa" represent "gram", "milliliter", "mole per liter", "Celsius degree" and "megapascal", respectively.

The following experimental conditions were employed in the examples below to determine X-ray diffraction patterns of pemetrexed diacid:
PW1710 BASED X-ray diffractometer
CuKα source (λ=1.5406 Å)
tube voltage: 30 kV
tube current: 30 mA
receiving slit: 0.05
scanning step: 0.1
step time: 2 s Example 1

The preparation of crystalline form H of pemetrexed diacid.

5 g of pemetrexed disodium (dry product) was dissolved in 50 ml of water. Then 60 ml of ethanol was added and pH value was adjusted to 1.5-2.0 with 2 mol/L HCl aqueous solution. The reaction mixture became clear when heating. Then, crystallization was carried out with stirring at room temperature for 1.5 hr. The solid was filtered and washed with appropriate amount of water (pH 4-5). Then the solid was dried at 45~50° C. under reduced pressure (0.085~0.090 MPa) for 30 hr to obtain 2.9 g of crystalline form H of pemetrexed diacid with water content of 7.1%.

For pemetrexed diacid prepared in this example, the position of diffraction peaks at 2θ are at 5.4°, 6.3°, 9.8°, 10.6°, 12.1°, 16.1°, 17.1°, 18.1°, 19.0°, 19.8°, 21.1°, 22.6°, 23.7°, 24.4°, 25.1°, 25.8°, 26.5°, 27.8°, 30.1°, 31.1°, 32.4°, and 38.5° (relative intensity above 10%), as measured by X-ray diffraction.

Example 2

The preparation of crystalline form H of pemetrexed diacid.

8 g of pemetrexed disodium (wet product) was dissolved in 24 ml of water. Then 24 ml of ethanol was added and pH value was adjusted to 2.0-2.5 with 1 mol/L HCl aqueous solution. The reaction mixture became clear when heating, and 36 ml of water was further added. Then, crystallization was carried out with stirring for 0.5 hr. The solid was filtered and washed with appropriate amount of water to obtain crystalline form H of pemetrexed diacid with water content of about 75%.

Figure 1:
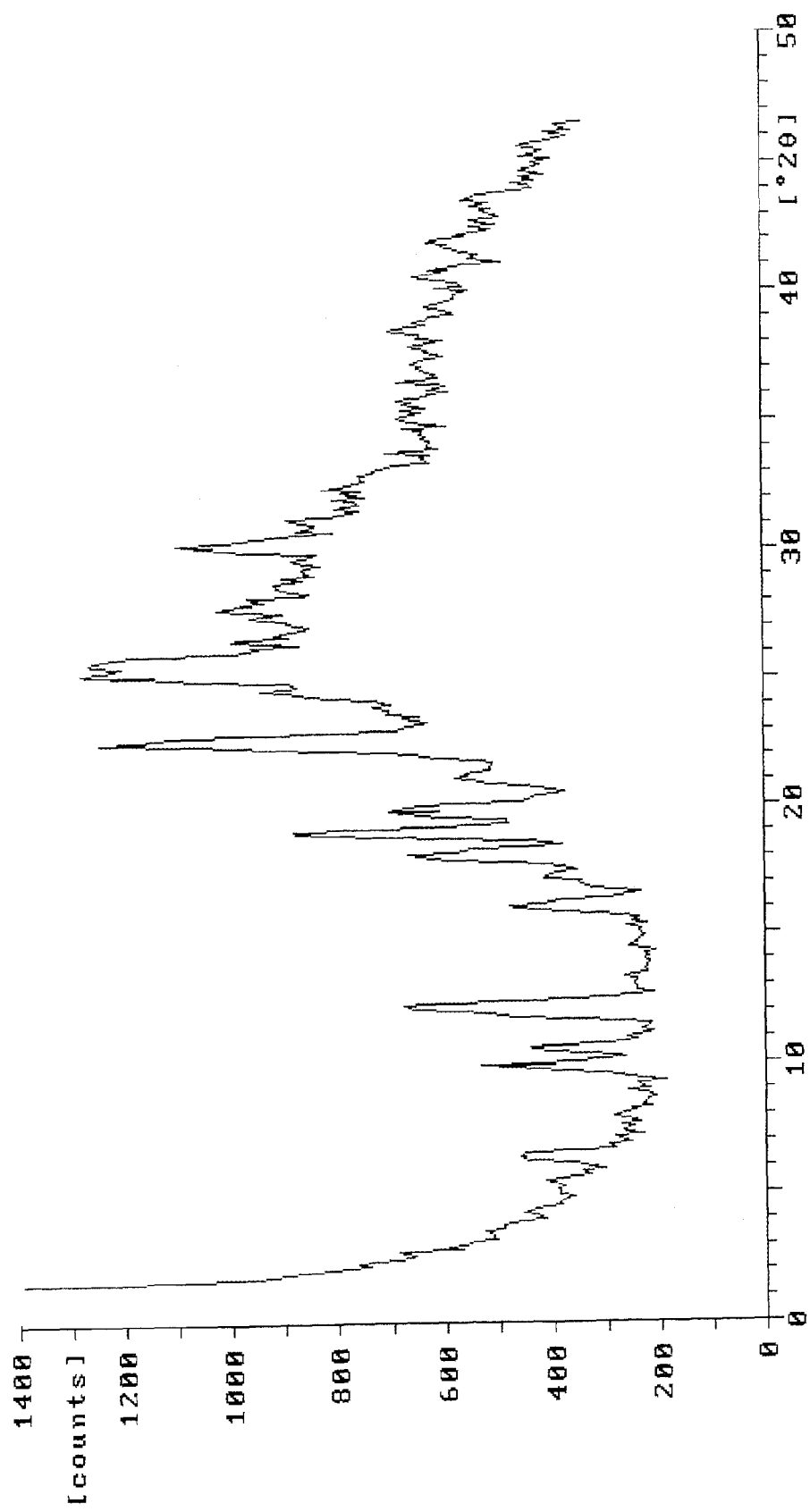
FIG. 1 shows X-ray powder diffraction pattern of crystalline form H of pemetrexed diacid.

For pemetrexed diacid prepared in this example, the position of diffraction peaks at 2θ are at 6.4°, 9.9°, 10.6°, 12.2°, 16.1°, 17.1°, 18.1°, 18.9°, 19.8°, 21.1°, 22.6°, 25.1°, 25.8°, 27.8° and 30.1°, as measured by X-ray diffraction. It has an X-ray powder diffraction pattern as shown in FIG. 1.

Example 3

The preparation of crystalline form H of pemetrexed diacid.

5 g of pemetrexed disodium (dry product) was dissolved in the mixture of 75 ml of water and 70 ml of acetone. The pH value was adjusted to 1.5-2.0 with 1.5 mol/L HCl aqueous solution. The reaction mixture became clear when heating. Then, crystallization was carried out with stirring for 1 hr. The solid was filtered and washed with appropriate amount of water. The solid was dried under reduced pressure (0.090~0.095 MPa) at 55~60° for 15 hr to obtain 3.2 g of crystalline form H of pemetrexed diacid with water content of 8.5%.

Pemetrexed diacid prepared in this example was identified as crystalline form H by X-ray diffraction.

Example 4

The preparation of crystalline form I of pemetrexed diacid.

10 g of pemetrexed disodium (dry product) was dissolved in 500 ml of water, and cooled to 0-5°. The pH value was adjusted to 4-5 with acetic acid and then adjusted to 2-3 with HCl aqueous solution. The reaction mixture was stirred for further 0.5 hr. The solid was filtered and washed with appropriate amount of water to obtain crystalline form I of pemetrexed diacid with water content of about 65%.

Figure 2:
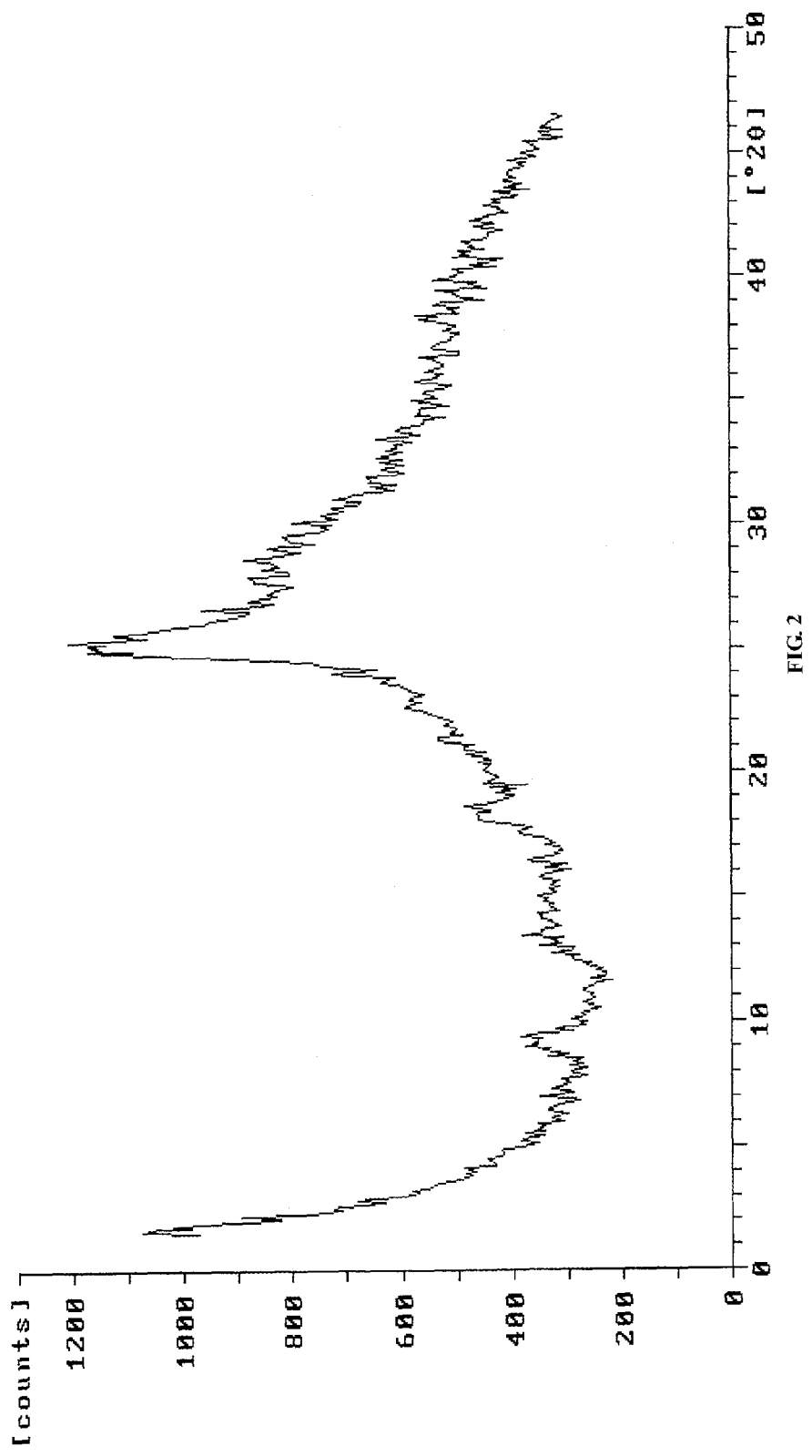
FIG. 2 shows X-ray powder diffraction pattern of crystalline form I of pemetrexed diacid.

Pemetrexed diacid prepared in this example has an X-ray diffraction pattern as shown in FIG. 2, as measured by X-ray diffraction.

Example 5

The preparation of crystalline form I of pemetrexed diacid.

10 g of pemetrexed disodium (wet product) was added in the mixture of 400 ml of water and 100 ml of ethanol. The pH value was adjusted to 11-12 with 4 mol/L NaOH solution with stirring, and then adjusted to 2-3 with 2 mol/L HCl solution followed by stirring for another 1 hour. The solid was filtered and washed with appropriate amount of water. Then the solid was dried under reduced pressure (0.085~0.090 MPa) at 45~50° for 35 hr to obtain 3.7 g of crystalline form I of pemetrexed diacid with water content of 6.7%.

Pemetrexed diacid prepared in this example was identified as crystalline form I, as measured by X-ray diffraction.

Example 6

The preparation of crystalline form J of pemetrexed diacid.

15 g of pemetrexed disodium (dry product) was dissolved in 375 ml of water with stirring, and cooled to 0-5°. The pH value was adjusted to 3-4 with acetic acid and the reaction mixture was further stirred for about 10 min. The solid was filtered and washed with appropriate amount of water. The solid was dried under reduced pressure (0.090~0.095 MPa) at 60-65° for 24 hr to obtain 12.1 g of crystalline form J of pemetrexed diacid with water content of 7.7%.

For pemetrexed diacid prepared in this example, the position of diffraction peaks at 2θ are at 8.8°, 12.1°, 17.2°, 18.3°, 19.4°, 20.2°, 21.1°, 23.1°, 24.3°, 26.2°, 27.6°, 28.8°, 30.0°, 31.6°, 32.7°, 34.1°, 34.8°, and 37.6° (relative intensity above 10%), as measured by X-ray diffraction.

Example 7

The preparation of crystalline form J of pemetrexed diacid.

15 g of pemetrexed disodium (wet product) was dissolved in 100 ml of water with stirring, then 40 ml of ethanol was added. Then pH value was adjusted to 2-3 with 1 mol/L HCl and the reaction mixture was further stirred for about 0.5 hr. The solid was filtered and washed with appropriate amount of water to obtain crystalline form J of pemetrexed diacid with water content of about 50%.

Figure 3:
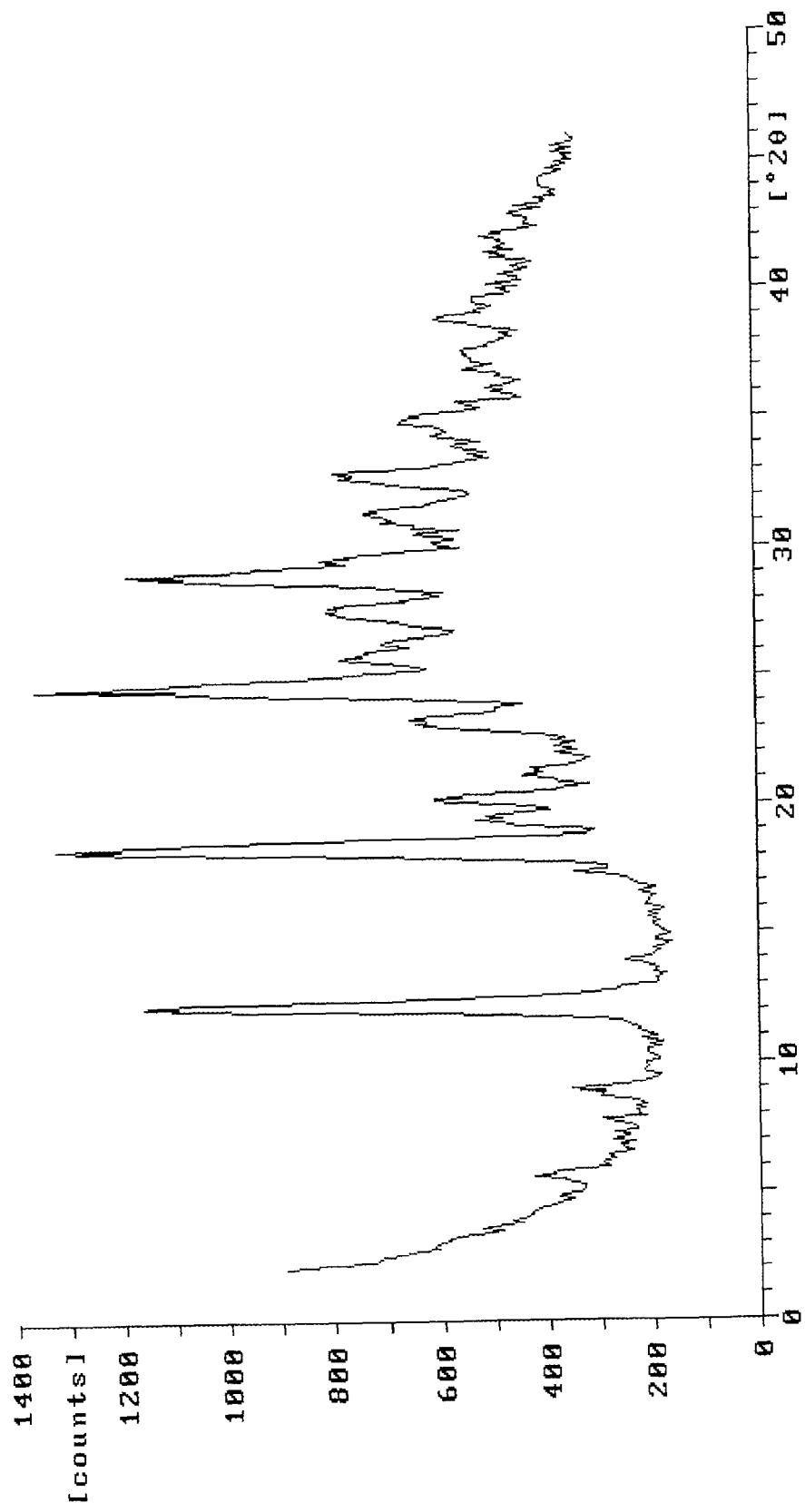
FIG. 3 shows X-ray powder diffraction pattern of crystalline form J of pemetrexed diacid.

For pemetrexed diacid prepared in this example, the position of diffraction peaks at 2θ are at 5.6°, 8.9°, 12.2°, 18.4°, 19.5°, 20.3°, 21.3°, 23.3°, 24.5°, 25.7°, 27.7°, 28.9°, 31.4°, and 32.8°, as measured by X-ray diffraction. The diffraction pattern is shown in FIG. 3.

Example 8

The preparation of crystalline form J of pemetrexed diacid.

10 g of pemetrexed disodium (dry product) was dissolved in 100 ml of water with stirring, then 100 ml of acetone was added. The pH value was adjusted to 3-4 with 2 mol/L HCl. The system was heated to 60~65° with stirring for about 10 min after a large amount of solid was precipitated. The reaction mixture was cooled with further stirring for about 1.5 hr. The solid was filtered and washed with appropriate amount of water to obtain crystalline form J of pemetrexed diacid.

Pemetrexed diacid prepared in this example was identified as crystalline form J as measured by X-ray diffraction.

Example 9

The preparation of pemetrexed disodium.

5 g of new crystalline form of pemetrexed diacid (dry product) prepared in the examples above was added in the 35 ml of water. The pH value was adjusted to 11-12 with 5 mol/L NaOH aqueous solution. The solution was stirred to improve dissolution, and then the pH was adjusted to 8-9 with 2 mol/L HCl. The reaction mixture was heated to 40~45°, 170 ml of acetone was added. The solution was cooled to crystallize with further stirring for about 1.5 hr. The solid was filtered and washed with appropriate amount of acetone. The solid was dried under reduced pressure (0.090~0.095 MPa) at 50° for 24 hr to obtain 5.3 g of pemetrexed disodium.

Example 10

The preparation of pemetrexed disodium.

7 g of new crystalline form of pemetrexed diacid (wet product) prepared in the examples above was added in 10 ml of water. The pH value of the system was adjusted to 10-11 with 5 mol/L NaOH solution and the solution was stirred to improve dissolution. 44 ml of acetonitrile was added. The solution was stirred at room temperature for about 2 hr to crystallize. The solid was filtered and washed with appropriate amount of acetonitrile/water mixture, as well as acetone to obtain pemetrexed disodium.

Example 11

The preparation of lyophilized pemetrexed disodium.

10.8 g of new crystalline form of pemetrexed diacid (dry product) prepared in the examples above was dissolved in 180 ml of water for injection. The pH value was adjusted to 11-12 with 2 mol/L NaOH solution. The solution was stirred to improve dissolution, and then the pH was adjusted to 7.0-8.5 with 2 mol/L HCl. The solution was made up to 250 ml, and then stirred for 10 min after adding 10.0 g of mannose and 0.05% activated carbon. The solution was filtered, and the filtrate was filled in vials for lyophilization in 12.5 ml/vial after sterile filtration to obtain pemetrexed disodium.

New crystalline forms mean crystalline forms H, I, J, or the mixture thereof in Examples 9-11.

The invention has been described above in detail, including preferred embodiments thereof. However, it should be noted that one skilled in the art could make modifications and/or variations upon the present invention without departing from the principle thereof. These modifications and variations should be regarded to be included within the scope of the attached claims.

The invention claimed is:

1. Crystalline form H of pemetrexed diacid, wherein the X-ray powder diffraction pattern thereof shows diffraction peaks at the following positions at 2θ: 9.9°, 12.2°, 16.1°, 18.9°, 19.8°, 22.6° and 25.1°.

2. Crystalline form H of pemetrexed diacid according to claim 1, characterized in that the range of water content thereof is 5 wt %~80 wt %.

3. A method for preparing crystalline form H of pemetrexed diacid, comprising crystallizing pemetrexed diacid from the mixed solution containing pemetrexed diacid, water and water-miscible solvent, the method including:

dissolving pemetrexed salt in a mixed solvent consisting of water and water-miscible solvent, and adjusting pH value thereof to 1-2.5 to crystallize pemetrexed diacid.

4. A method for preparing a pharmaceutically acceptable salt of pemetrexed diacid, comprising reacting the crystalline form of pemetrexed diacid according to claim 1 with corresponding alkali.

5. The method according to claim 4, wherein the use of the crystalline form of pemetrexed diacid in the preparation of a pharmaceutically acceptable salt of pemetrexed diacid through reaction with corresponding alkali comprises:

adding pemetrexed diacid in an aqueous solvent, dissolving pemetrexed diacid with corresponding alkali; adding appropriate organic solvent miscible with water after dissolution to precipitate a pharmaceutically acceptable salt of pemetrexed diacid; or performing directly lyophilization to obtain a pharmaceutically acceptable salt of pemetrexed diacid in freeze-dried form; wherein the aqueous solvent includes water, and mixed solvent of water and organic solvent miscible with water.

6. The method according to claim 4, wherein the corresponding alkali is sodium hydroxide, and the pharmaceutically acceptable salt of pemetrexed diacid is pemetrexed disodium.

7. The method according to claim 5, wherein the corresponding alkali is sodium hydroxide, and the pharmaceutically acceptable salt of pemetrexed diacid is pemetrexed disodium.

* * * * *